US007026600B2

(12) United States Patent
Jamieson et al.

(10) Patent No.: US 7,026,600 B2
(45) Date of Patent: Apr. 11, 2006

(54) SYSTEM AND METHOD OF IDENTIFYING AN OBJECT IN A LASER BEAM ILLUMINATED SCENE BASED ON MATERIAL TYPES

(75) Inventors: James R. Jamieson, Savage, MN (US); Mark D. Ray, Burnsville, MN (US); Clinton T. Meneely, Burnsville, MN (US)

(73) Assignee: Rosemount Aerospace Inc., Burnsville, MN (US)

( * ) Notice: Subject to any disclaimer, the term of this patent is extended or adjusted under 35 U.S.C. 154(b) by 157 days.

(21) Appl. No.: 10/789,114

(22) Filed: Feb. 26, 2004

(65) Prior Publication Data

US 2005/0189503 A1    Sep. 1, 2005

(51) Int. Cl.
*H01J 40/14*    (2006.01)

(52) U.S. Cl. .................................. 250/221; 250/559.4

(58) Field of Classification Search ...................... None
See application file for complete search history.

(56) References Cited

U.S. PATENT DOCUMENTS

| 5,835,199 | A |   | 11/1998 | Phillips et al. |
| 6,139,323 | A | * | 10/2000 | Christians et al. ............. 434/16 |
| 6,542,227 | B1 |   | 4/2003 | Jamieson et al. |
| 2003/0043364 | A1 |   | 3/2003 | Jamieson, et al. |

FOREIGN PATENT DOCUMENTS

EP    0 431 299    6/1991

OTHER PUBLICATIONS

HARDIE, et al., Spectral Band Selection and Classifier Design for a Multispectral Imaging Laser Radar, Optical Engineering, Soc of Photo- optical Instrumentation Engineers, vol.37, no. 3, pp. 752-762, Mar., 1998.
European Seach Report from European patent application no. EP05251141.

* cited by examiner

*Primary Examiner*—Que T. Le
(74) *Attorney, Agent, or Firm*—Calfee, Halter & Griswold LLP; Peter Hernandez, Esq.

(57) ABSTRACT

A method of identifying an object in a laser beam illuminated scene based on material types comprises the steps of: emitting a pulsed beam of laser energy, each beam pulse comprising a plurality of different discrete wavelength emission components; illuminating a predetermined scene with the pulsed beam; receiving return laser pulses from objects within the illuminated scene, each return laser pulse comprising return components corresponding to the plurality of different discrete wavelength emission components; determining spectral reflectance values for the plurality of return components of each return laser pulse; determining a material type for each return laser pulse of the illuminated scene based on the plurality of reflectance values of the corresponding return pulse; indexing each determined material type to a position in the illuminated scene; and identifying an object in the illuminated scene based on material types and indexed positions thereof in the scene. A counterpart system for carrying out the method is also disclosed.

43 Claims, 12 Drawing Sheets

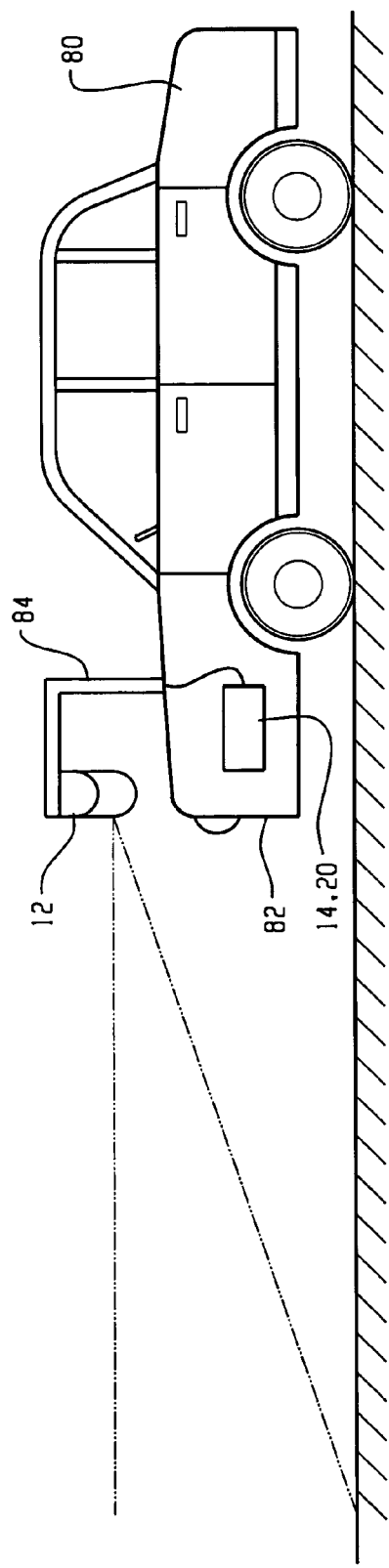
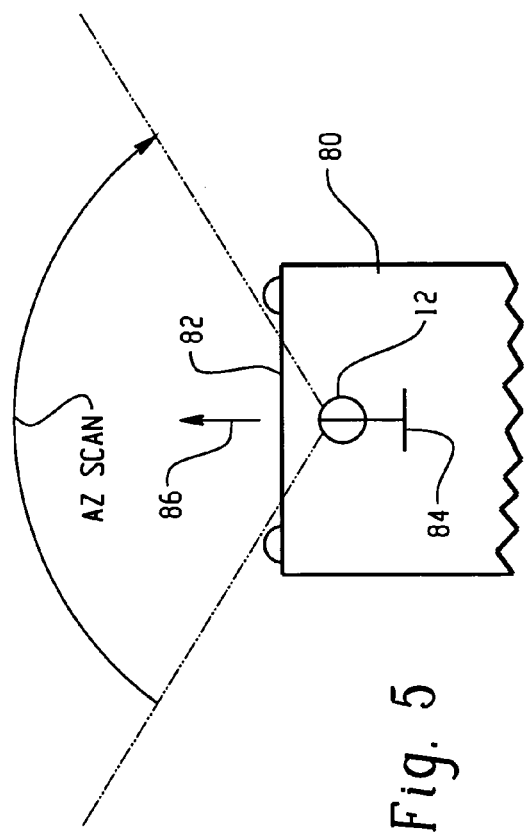
Fig. 4
Fig. 5

SYSTEM AND METHOD OF IDENTIFYING AN OBJECT IN A LASER BEAM ILLUMINATED SCENE BASED ON MATERIAL TYPES

BACKGROUND OF THE INVENTION

The present invention is related generally to the detection of threats to a target using active laser technologies, and more particularly, to an active laser system and method of identifying and classifying an object in a laser beam illuminated scene based on material types.

Mobile military forces can operate in a wide range of environments. These environments can be varied in material types such as naturally occurring sand and vegetation to snow; urban areas with vehicles and buildings; or mountainous terrain. In all cases, man-made or naturally occurring materials radiate reflected and emitted energy based on internal and external sources. Hot objects, for example, radiate heat, a process that can be exploited by passive thermal imagers to discriminate against a cooler background. However, this detection is merely an indication of a thermal gradient. No information is necessarily available on the type of thermal gradient detected.

Primary threats from military adversaries are well understood and developed. Today, the threats to mobile military forces have been reduced to perimeter zones that currently are not served by radar, passive IR sensing systems, or visual identification. Even the most sophisticated passive IR sensors and active radar cannot automatically classify a wide range of targets or such a diverse area as described herein. Current unattended sensors have notoriously high false alarm rates due to the inability to capture enough information necessary to make an intelligent decision. With today's technology, sensing systems might falsely identify a dog as a threat, wasting valuable time and attention.

Passive multi-spectral sensing systems rely on reflected sunlight to view given areas of land. Such systems have been used on space based geographic (LANDSAT, SPOT) and weather satellites (NIMBUS, GOES), for example. Typically, the reflected sunlight is received from the land and passed through a series of band pass filters or a filter wheel to look at radiance at a specific wavelengths. This detection scheme is limited to discrete spectral bands and prescribed by the filter transmission bands. Further, since these passive systems rely on reflected sunlight, the presence of clouds and infrared thermal emissivity can affect and alter the passively collected energy. As such, sophisticated calibration schemes and ground truthing are required to properly determine the scene radiance for the given area of land.

Similarly, there have been extensions to this basic passive multi-spectral sensing technology. One such extension operates through use of a Michelson Interferometer to decompose the reflected sunlight into thousands of channels. This extension is commonly referred to as hyperspectral sensing and employs thousands of spectral channels deconvoluted from the interferometric data using intensive data processing techniques. As with the basic technology, the hyperspectral sensing approach also requires extensive calibration and is often not well suited for battlefield environments.

To overcome the drawbacks of today's sensing systems that include video, infrared imaging, and passive multi-spectral and hyper-spectral sensing, for example, an active laser system for detecting threats around a perimeter of a target has been disclosed in the co-pending U.S. patent application Ser. No. 10/440,918, filed May 19, 2003, and entitled "Laser Perimeter Awareness System" which is assigned to the same assignee as the instant application. This laser perimeter awareness system (LPAS) is based on core technologies of a laser object awareness system (LOAS) disclosed in the U.S. Pat. No. 6,542,227, issued Apr. 1, 2003, which is also assigned to the same assignee as the instant application. Both of the aforementioned documents are hereby incorporated by reference in their entirety into the instant application for providing more structural and operational details of such systems which may not be afforded by the instant application.

Both LPAS and LOAS use a single channel, scanning, eye-safe laser operating at a wavelength of approximately 1.55 microns. The LOAS was developed primarily to enable helicopters and unmanned aircraft vehicles (UAVs) to detect and avoid power lines and other ground structures. The LPAS, which is a variant of the LOAS, is capable of detecting and isolating swimmers in the water, moving vehicles, and persons at ranges spanning several meters to two kilometers down range. Longer ranges are possible by increases in optical performance and emitted laser energy. By exploiting the laser returns from an object and comparing them to high resolution laser baseline information, LPAS is capable of rendering awareness of only objects moving on the ground within a perimeter while ignoring the background clutter. Also, in LPAS, raw laser return data may be used in concert with visible or IR camera images for shape classification and alarm cueing in an integrated and autonomous environment.

With LPAS, it is possible to detect and determine range, bearing and elevation of moving and newly appearing objects and to determine threat potential to a target at which LPAS is located using shape feature classification and well defined constant bearing decreasing range (CBDR) algorithms. However, LPAS can not establish objects that are different than those expected in the naturally occurring or urban environment.

While LOAS, LPAS, and other laser or conventional radar systems provide object detection, they do not provide the real intelligence in order to classify the type of threat which is desirable to aid military forces operating in the wide range of environments. Of particular importance is the ability of an active laser system to detect and classify threats in heavily urban or mountainous environments at short ranges. This is critical today as military forces pursue non-combatants in urban and rural environments. A laser sensing system which will bring to the warfighter a capability to know his or her threat environment long before the enemy can take action will create an overwhelming position of dominance.

The present invention is intended to improve upon the LPAS and provide a laser sensing system capable of detecting and classifying the type of threat which will aid military forces operating in the wide range of environments, especially in heavily urban or mountainous environments. Likewise, it eliminates significant cost, complexity, and weight of passive sensors, such as cameras, infrared sensors, and multi-spectral and hyper-spectral devices.

SUMMARY OF THE INVENTION

In accordance with one aspect of the present invention, a method of identifying an object in a laser beam illuminated scene based on material types comprises the steps of: emitting a pulsed beam of laser energy, each beam pulse comprising a plurality of different discrete wavelength emission components; illuminating a predetermined scene with the pulsed beam of laser energy; receiving return laser pulses from objects within the illuminated scene, each return laser pulse comprising return components corresponding to the plurality of different discrete wavelength emission components; determining spectral reflectance values for the plurality of return components of each return laser pulse; determining a material type for each return laser pulse of the illuminated scene based on the plurality of reflectance values of the corresponding return pulse; indexing each determined material type to a position in the illuminated scene; and identifying an object in the illuminated scene based on material types and indexed positions thereof in the scene.

In accordance with another aspect of the present invention, a system for identifying an object in a laser beam illuminated scene based on material types comprises: a laser source for emitting a pulsed beam of laser energy, each beam pulse comprising a plurality of different discrete wavelength emission components; a first arrangement of optical elements disposed in a path of the pulsed beam for illuminating a predetermined scene with the pulsed beam of laser energy; a second arrangement of optical elements for receiving return laser pulses from objects within the illuminated scene and separating each return laser pulse into return components corresponding to the plurality of different discrete wavelength emission components; a first processing circuit for receiving the return components, determining spectral reflectance values for the plurality of return components of each return laser pulse, and generating reflectance signals representative thereof; and a second processing circuit for receiving the reflectance signals and determining a material type for each return laser pulse of the illuminated scene based on the plurality of reflectance signals of the corresponding return pulse, the second processing circuit operative to index each determined material type to a position in the illuminated scene, and to identify an object in the illuminated scene based on material types and indexed positions thereof in the scene.

BRIEF DESCRIPTION OF THE DRAWINGS

FIGS. 4 and 5 are side and top view illustrations, respectively, of a vehicle suitable for use as a moving platform for the laser system embodiment of FIG. 1.

DETAILED DESCRIPTION OF THE INVENTION

Figure 1:
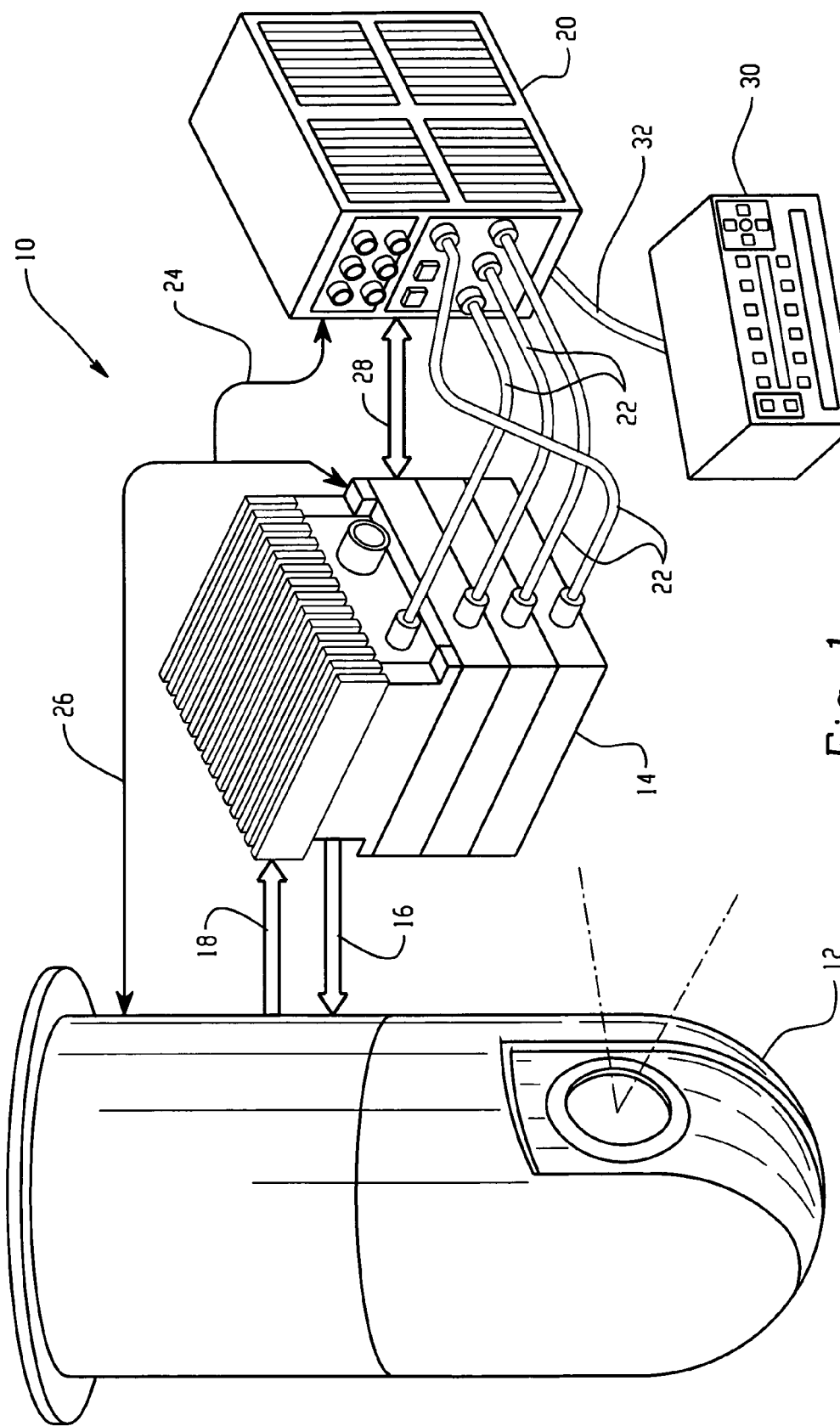
FIG. 1 is an illustration of an active laser system suitable for embodying the broad principles of the present invention.

One aspect of the present invention involves the seamless data fusion of range-resolved laser data imagery with multi-spectral near-infrared (IR) reflectance data. Unlike passive remote sensors, the multi-spectral reflectance data image is formed through active laser illumination of a target area simultaneously at a plurality of discrete wavelengths or wavelength bands. By exploiting the near-infrared absorption and reflectance characteristics of different materials using an active laser source, dependencies on sunlight are eliminated. The laser system of the present invention will be of sufficient spatial and spectral resolution to resolve the fine material details such as the metal barrel of a rifle against the clothing fabric of a non-combatant hundreds of meters down range. This may be accomplished for stationary and moving scenarios.

In the present system, a single, compact scanning laser system will simultaneously emit pulses of laser light at a plurality of wavelengths creating a multi-spectral cube or multi-dimensional array of near-infrared reflectance values. Ranging, ground motion detection, and near-IR reflectance measurements at several critical wavelengths will be used in conjunction with Automatic Target Recognition (ATR) techniques to identify suspected threats of interest. The ATR techniques may use an artificial intelligence neural network algorithm or similar algorithmic schemes, for example, to classify pixel by pixel material features in the image scene based on the relationships of near-infrared reflectance measurement values. Other classification techniques may also be used such as adaptive genetic algorithms to enhance learning in the field. Ground truth information may be established for training the neural network algorithm and identifying threats. Based on the near-IR multi-spectral reflectance data and ranking of processed threats, a geo-located threat priority may be presented to a military crew or ground forces for disposition using easily interpreted display symbology and a user interface.

This information, tightly coupled with moving ground object indication in a geo-located reference frame, will further aid in classifying threats and intent. This may be accomplished in the present system by referencing real-time, raw laser radar returns with geo-located background clutter maps, Constant Bearing Decreasing Range (CBDR) data, and geo-referenced maps or satellite imagery. Differencing schemes will be used to discern ground motion by comparing real-time data to the previously collected clutter maps in an automated environment. A basic moving ground object indication for stationary laser radar sensing has been developed in the LPAS which is disclosed in the co-pending U.S. application Ser. No. 10/440,918 which has been incorporated by reference herein.

Using the moving ground object indication techniques of LPAS in conjunction with the range resolved, multi-spectral reflectance measurement data, real-time coordinate transformations may be used to compensate for changes in the spatial positioning of the active laser sensor using Global Positioning System (GPS) and inertial navigation inputs. Through this compensation of vehicle or ship motion, the multi-spectral reflectance data may be referenced to a geo-located reference frame suitable for use on a moving ground vehicle or surface ship. The multi-spectral reflectance data may be merged with pre-stored digital terrain elevation data to further remove or augment land features which will permit not only material identification and classification on a pixel by pixel basis, but also range resolved moving ground object indication while the sensor is in motion on the ground vehicle or ship.

The use of a plurality of carefully-chosen near-infrared wavelengths to form the multi-spectral reflectance data image scene in real-time simplifies the enormous task and complexity of data reduction often associated with passive hyper-spectral and multi-spectral imaging. Because the measuring sensor is active, rather than passive, this aspect of the present invention will work equally well in full sun or under cloud cover, as well as night operations. Further, by exploiting the near-IR band, spectral signatures are outside the range of conventional silicon based detectors. Thus, detectability coupled with the low probability of intercept/low probability of detection results in significant reductions in emitted signatures when compared to short range RF and mm-wave radar systems. The multi-spectral, range-resolved reflectance data will enable intelligent information regarding moving ground objects, either on land or at sea, from stationary or moving platforms. This unmatched capability will afford a higher degree of confidence and early warning essential to operate in today's threat environment.

The present sensing system does not depend on the sun for illumination, but rather uses a scanned laser beam with a plurality of very narrow or discrete wavelengths. Thus, the system is usable day or night. This also means that the angle between the illuminating laser source and the receiver is constant, i.e. zero degrees. In conventional hyper-spectral instruments, corrections must constantly be made for sun-target-receiver angle.

In addition, some optical receivers may use a moderately narrow-band filter to minimize background optical noise, but the bandwidth of the laser beam actually determines the spectral resolution of the system, which may be as narrow as 1 nanometer (nm) or less. Within this narrow bandwidth, the laser illumination is much more intense than typical solar illumination levels. In the 1.535–1.62 micron wavelength regions used by the present system, the earth's atmosphere is still moderately absorptive, which limits the optical range of the system somewhat, but limts the solar background in this region, thus enhancing the system's signal-to-noise ratio or SNR without requiring typically low transmission very narrow-band filters in the optical receiver.

Also, the present system may use a scanned spot to determine range and reflectance, rather than a focal plane detector that looks at the entire field of regard simultaneously. While this may slow the image update rate, the signal to noise ratio can be highly optimized within the narrow instantaneous field-of-view (IFOV). In addition, the time-of-flight range information collected for each pixel is another parameter that can be used to help discriminate object materials by congruity, i.e. two adjacent pixels in 3-D space with some similar spectral characteristics are probably the same material. If they are separated in range they may not be, even though they are side by side in a 2-D display.

In the present system, the number of spectral bands is limited by the number of laser lines available. In one embodiment of the present invention, only four laser lines in the C and L telecommunications bands are used, thus limiting the spectral information available. This is because current available eye-safe, fiber lasers use Erbium-glass amplifiers that only operate in this wavelength range. Other embodiments may easily use several additional lines at wider spectral separations to produce better threat discrimination.

Figure 11:
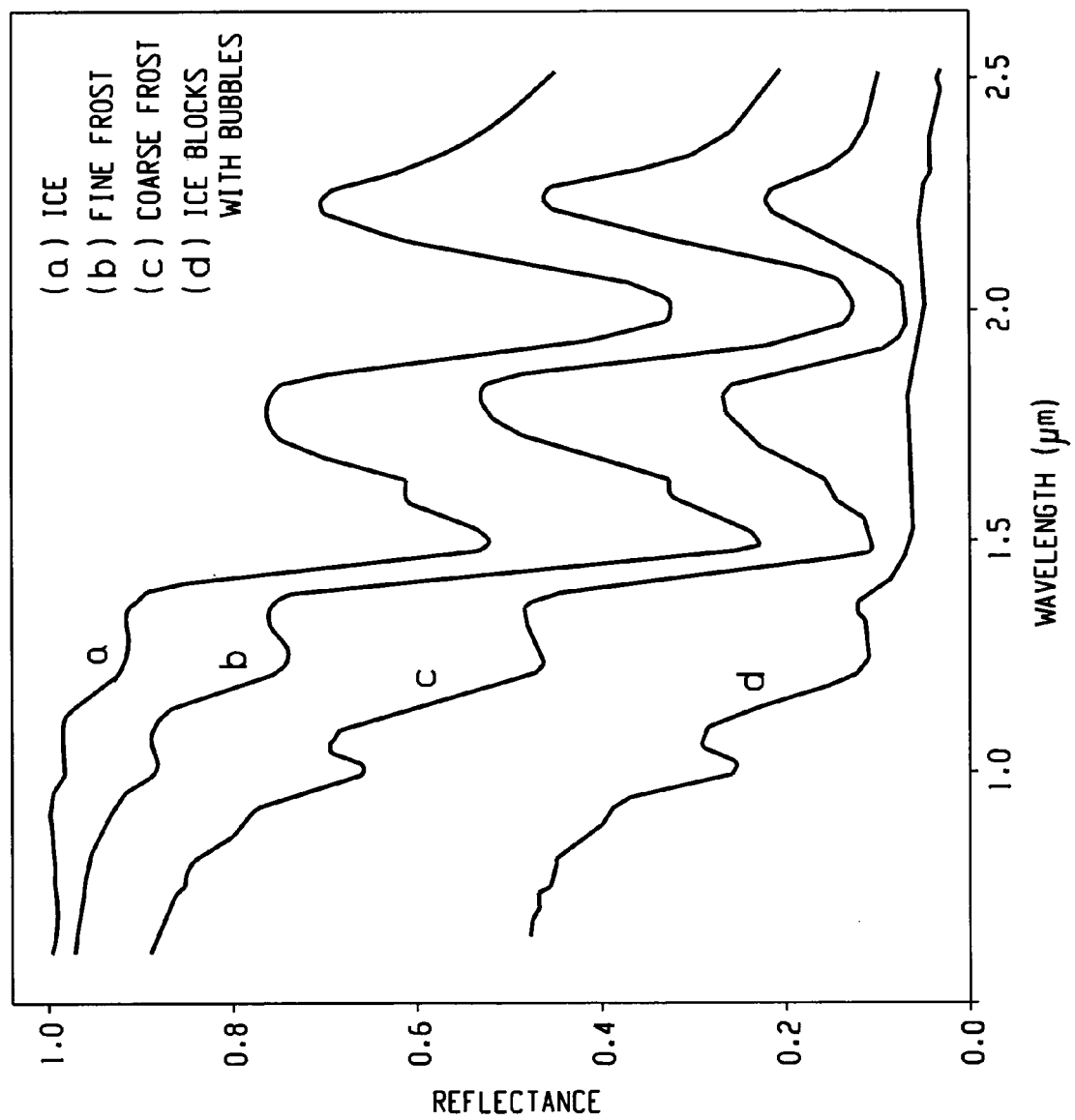
FIG. 11 is a graph of exemplary curves illustrating the effects of forms of water on reflectance values of wavelengths in the near infrared band.

A major factor in the 1.5 micron spectral region is the effect of water, which in liquid form exhibits a broad strong absorption peak centered around 1.45 microns as shown in FIG. 11. In fact, it is the edge of this water absorption that is largely responsible for the atmospheric losses mentioned earlier. Since most green vegetation is transmissive to the laser beam to some degree, this water absorption is a prominent feature of their spectral signatures. For ice, this absorption peak moves to slightly longer wavelengths. In addition, many minerals contain $OH^-$ ions which also absorb in the same regions. Therefore many of these minerals also exhibit a steep rise in reflectivity for longer wavelengths immediately above 1.5 microns. Other materials may exhibit flat reflectance spectra in this region, since they have no prominent absorption peaks nearby.

Figure 12:
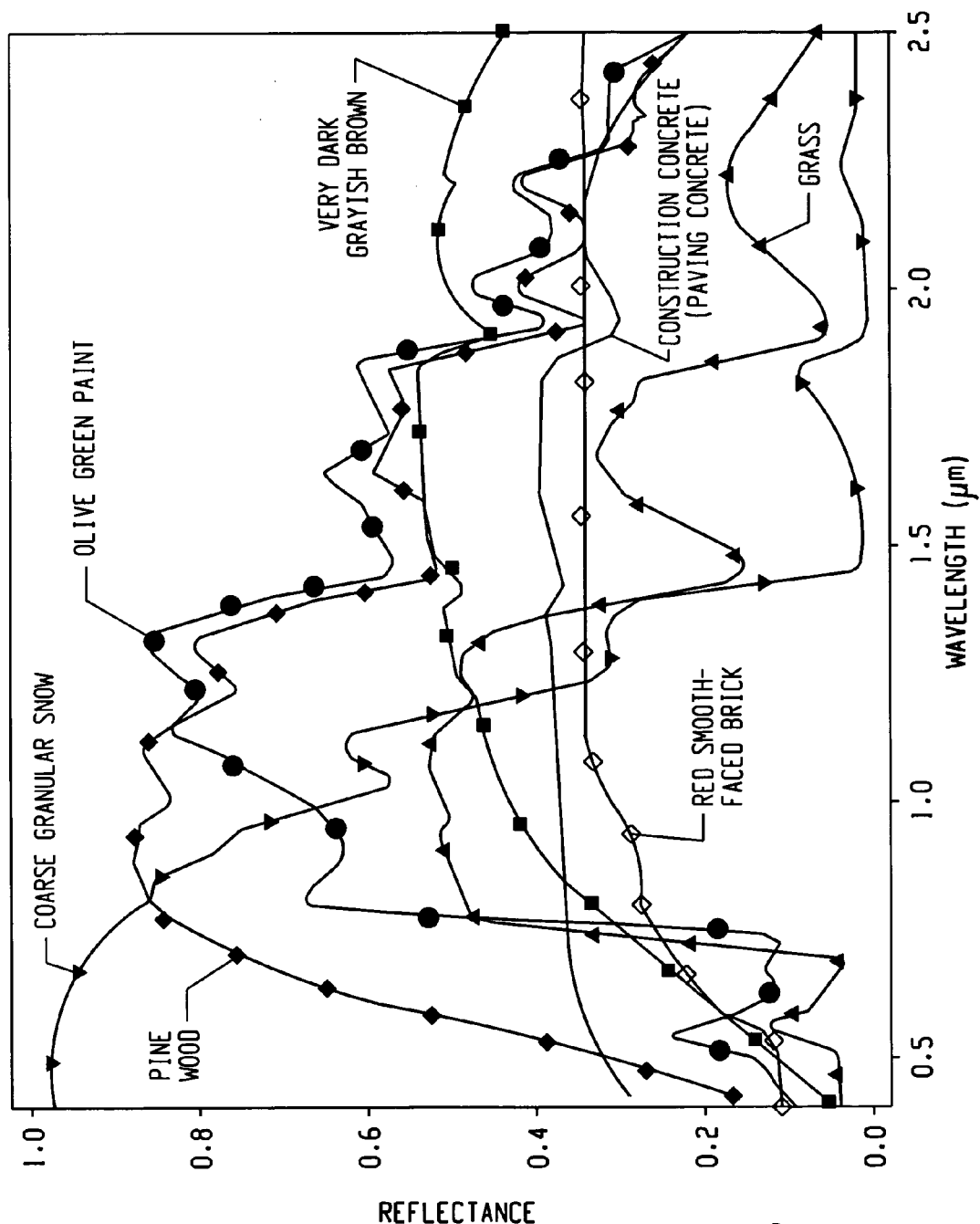
FIGS. 12 and 13 are graphs of curves exemplifying the reflectance spectra of different man-made and naturally occurring materials.
Figure 13:
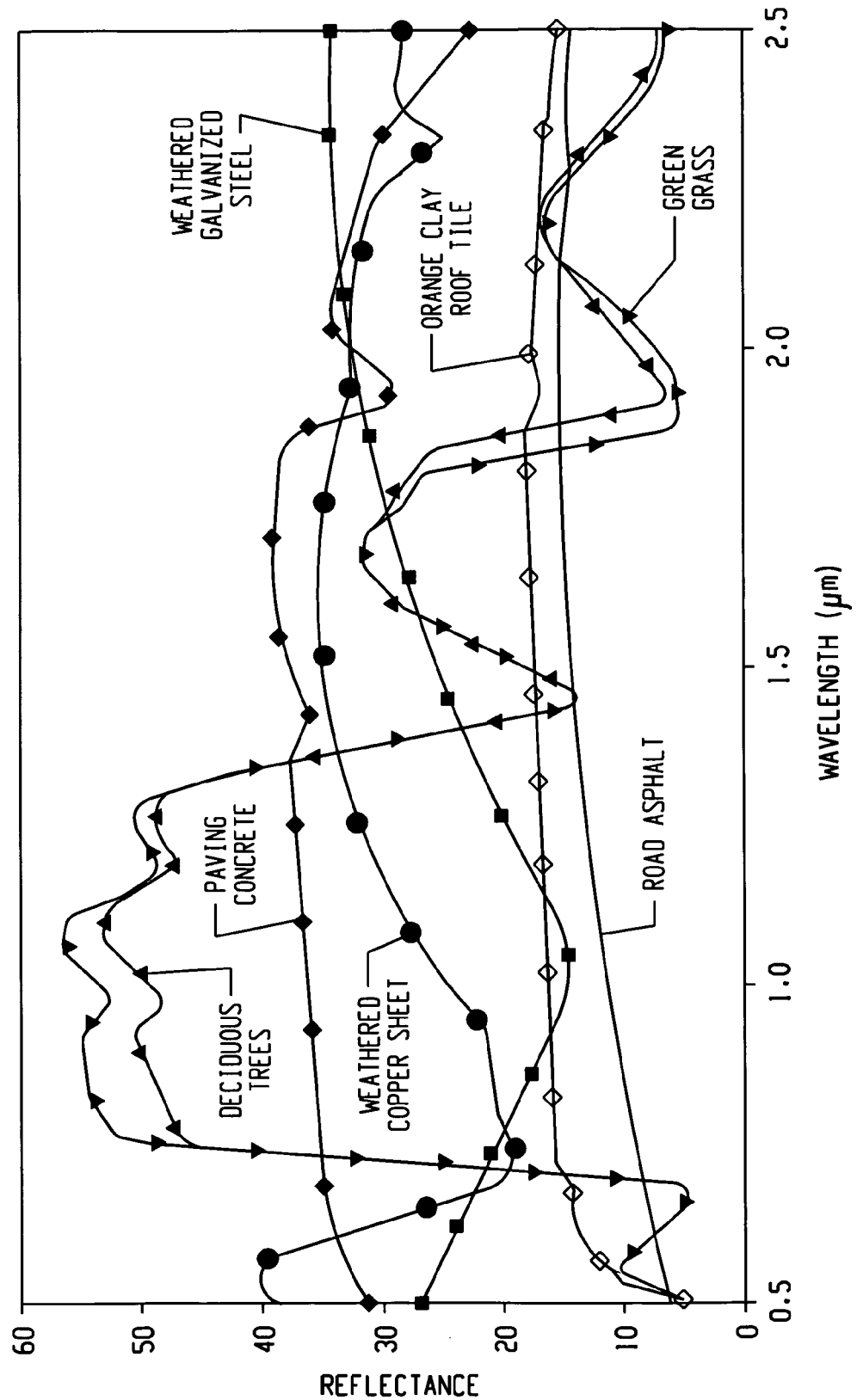

By measuring both the reflectance amplitude and spectral reflectance variation at the four laser bands for objects in the field of regard, many artificial materials can be distinguished from natural ones, even with this sparse data set. Examples of reflectance spectra of natural and selected man-made materials in the wavelength range from 0.4 to 2.5 microns are shown in FIGS. 12 and 13. Note that materials may be distinguished from one another by comparing a plurality of reflection values of each at selected different wavelengths.

FIG. 1 illustrates an exemplary active laser system 10 suitable for embodying the broad principles of the present invention. Referring to FIG. 1, the system 10 includes a laser scanning head 12 which may be similar to the type used in the LPAS disclosed in U.S. patent application Ser. No. 10/440,918 referenced above, for example. Also included in system 10 is a multi-spectral laser module 14 comprising a plurality of matched laser beam generation and reflectance detection channels or "slices". In the present embodiment, four slices are included in module 14, each tuned and matched to a different discrete laser wavelength, preferably within the near IR wavelength band of approximately one to two microns.

One of the four slices may be tuned to the 1.55 micron laser wavelength much the same as employed in the LPAS for object ranging and motion detection. Discrete laser wavelengths of the other three slices of module 14 are chosen in the near IR band, say from 1.06 to 2.0 microns, for example, to exploit the natural variations of reflectance and absorption of the surrounding environment/geographical region in which the system 10 is operating as noted above. The selection of the discrete wavelengths of the other three channels may be set to produce the greatest contrast between those objects likely found in the background clutter of the scanned laser illumination (e.g. sand, rocks, vegetation, etc.) and those objects within the laser scan that represent a potential threat (e.g. painted vehicles, clothing, metallic objects, and the like).

Discrete laser wavelengths of the slices of module 14 may be also selected on the ability to leverage existing telecommunication technologies based on fiber optic laser amplifiers using a master oscillator power amplifier (MOPA) architecture with laser pulse repetition rates exceeding 60 kHz, for example. As will be described in greater detail below, certain of the optical components of each slice of module 14 may be matched for tuning the wavelength of the laser beam generation with the wavelength of the corresponding reflectance sensing thereof. Such optical components may be constructed within each slice to be easily removable and/or interchangeable to permit experimentation and flexibility for operation of the system 10 in different environments and geographical regions. In this manner, each channel is tunable so as to effectively interrogate the spectrum of interest.

In the present embodiment, each slice of module 14 may include a laser source tuned to a selected wavelength in the near IR band as noted above. The four laser sources may be operated to emit their laser pulses simultaneously. The pulsed laser outputs of the four laser sources may be coupled over a common fiber optic cable 16 to the laser scanning head 12 which is operated to scan the pulsed laser beam comprising the four pulses of different wavelengths over a targeted area. Laser echoes returned from objects and clutter within the targeted scan area are received by the scanner 12 and returned to module 14 over another common fiber optic cable 18.

Module 14 includes a form of wavelength division multiplexing to segment the different wavelength echo or return pulses received from cable 18 into their corresponding slices for detection and downstream receiver processing. As described above, the magnitudes of these laser echoes are representative of reflectance values at the different discrete wavelengths used in system 10 for classifying potential threats based on the material make-up thereof. This process of classifying threats based on the reflectance values will become more evident from the description found herein below. Each slice of module 14 includes a light detector for detecting the return laser pulse at the designated wavelength and converting the light pulse into a corresponding electrical signal which may be additionally signal conditioned within the slice.

The conditioned electrical echo signals are conducted from the slices of module 14 to an electronics module 20 over separate signal lines 22 for further electronic signal processing which will be described in greater detail herein below. In addition, electrical power may be provided to both the scan head 12 and module 14 from the electronics module 20 over path 24 and signals representative of the azimuth (AZ) and elevation (EL) of the scanned beam may be supplied from the scan head 12 to the electronics module 20 via the module 14 over signal paths 26 and 28. A control panel 30 may be coupled to the electronics module 20 over path 32 for entering data and controlling the module 20 through training and calibration operations of the system 10 as will become more evident from the description below.

Figure 3:
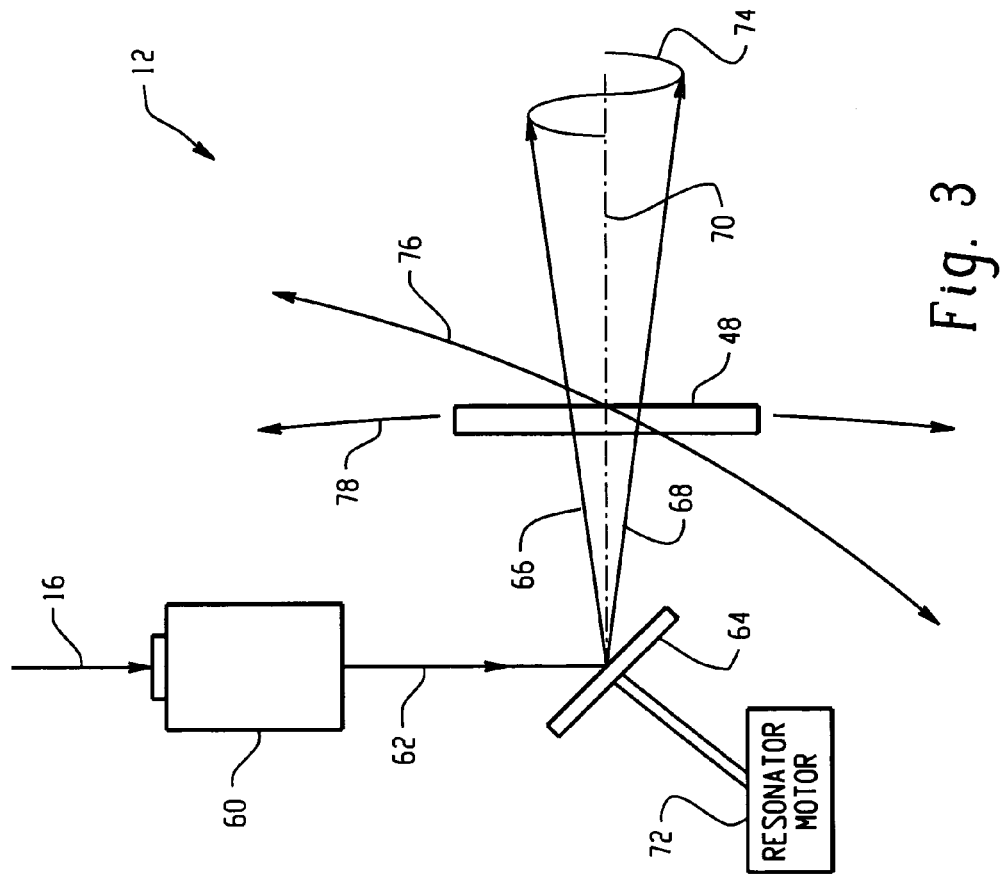
FIG. 3 is an illustration of an arrangement of optical components suitable for use in the scanning head embodiment of FIG. 2.
Figure 2:
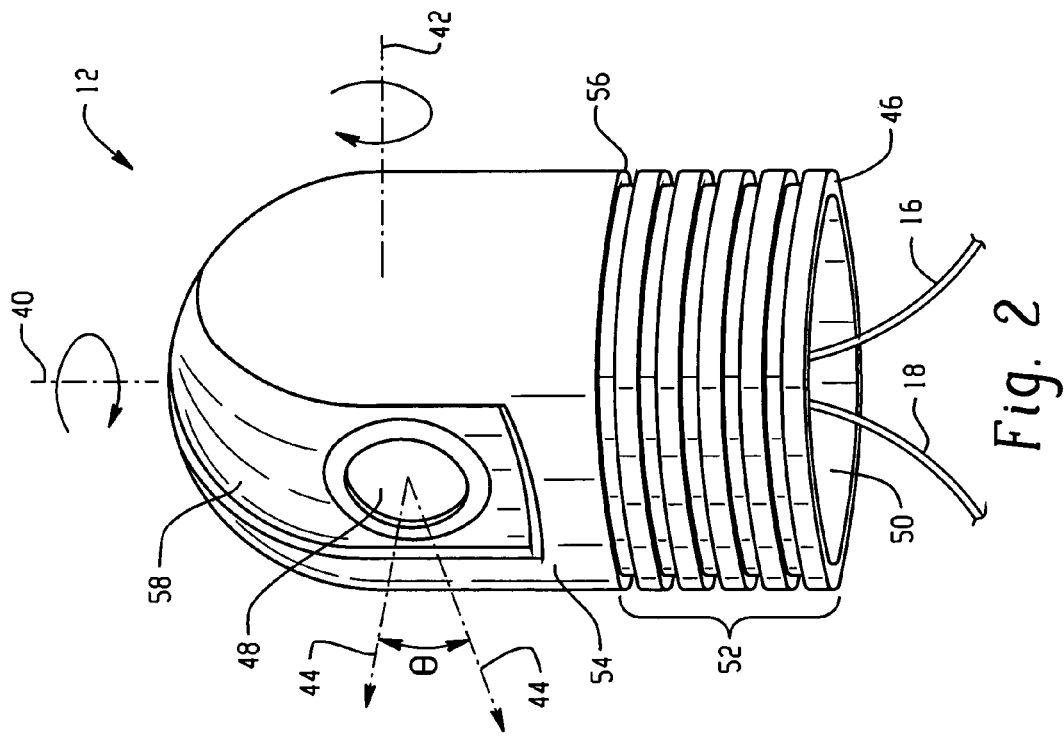
FIG. 2 is an illustration of a laser beam scanning head suitable for use in the embodiment of FIG. 1.

A laser beam scanning head suitable for use in the embodiment of FIG. 1 is illustrated in FIG. 2 and an exemplary embodiment of the optical components thereof is depicted in FIG. 3. Referring to FIG. 2, a scan head 12 controls the movement of an oscillating laser beam scan pattern at least along an azimuth axis 40 and an elevation axis 42. The extent of the laser beam oscillation in elevation angle θ is shown by the dot-dashed lines 44. A section 46 of the scan head 12 may be mounted to a structure of a sensor platform, which may be a moving vehicle, for example, such as shown in the sketches of FIGS. 4 and 5. A window area 48 of the scan head 12 through which the beam scans are emitted would be pointed in the direction of the corresponding target scan area. The fiber optic cable 16 carrying the pulsed laser energy from the laser sources of module 14, which will be described in greater detail herein below, may be passed into the scan head 12 through an opening 50 at the bottom of section 46 or through an opening in a side area 52 described below.

Optical elements within the scan head 12, which will be described in greater detail in connection with FIG. 3 below, cause the beams passed by the cable 16 to be oscillated in elevation through the scan angle θ. A conventional motor assembly (not shown) within the scan head 12 controls movement of another section 54 thereof through an azimuth scan angle about the axis 40 sufficient to cover the corresponding targeted area. This azimuth movement occurs along a seam 56 between the sections, 46 and 54 and effectively moves the oscillating laser beams along with the section 54 which projects the beam scan pattern through a sinusoidal pattern 74 as shown in FIG. 3.

Another section 58 of the scan head 12 which includes the window area 48 and falls within the portion 54 moves azimuthally with the portion 54. Another conventional motor (not shown) disposed within the scan head 12 controls movement of the portion 58 about the axis 42 permitting control of the oscillating laser beams in elevation, for example, which may extend the targeted area outward from or inward to the sensor platform. In the present embodiment, the window area 48 of the portion 58 may be controlled to rotate to a position inside the portion 54 to protect it from the environment when not in use. A corrugated skin or surface may be provided in the side area 52 to act as a heat sink to improve the transfer of heat away from the scan head 12 during operation thereof. Alternately, in the case where heat dissipation may not be needed by the drive systems of the scan head 12, the side area 52 may be smooth as shown in FIG. 1.

A sketch exemplifying the optical elements inside the scan head 12 is shown in FIG. 3. Referring to FIG. 3, the fiber optic cabling 16 may be aligned with the axis of the input aperture of a beam expander 60 to guide the laser beam therethrough. The expanded beam exiting the expander 60 over optical path 62 may be reflected from an oscillating mirror 64 over a scan of optical paths between path 66 and path 68 about a central axis 70. The oscillated laser beams exit the scan head 12 through the window 48. In the present embodiment, the oscillating mirror 64 may be driven by a mechanically linked resonant scanner unit 72 at an oscillation frequency of approximately one hundred hertz, for example. While the present embodiment uses a resonant scanner assembly for oscillating the laser beam, it is understood that other elements may be used for oscillating the laser beam, like a galvonometer-driven mirror, a transparent liquid crystal scanner or a microlens array scanner, for example, without deviating from the broad principles of the present invention.

As described herein above, return laser pulses or echoes follow a bi-static laser beam return path 18 which may be embedded in the fiber optic cable 16, for example. However, it is understood that laser beam echoes may follow the same optical scan paths as their emitted beams for return to the module 14 just as well. The window area 48 may comprise a clear, flat, zero power optical element made of a material like glass, for example, so as not to interfere substantially with the scan pattern of the exiting laser beams. In the present embodiment, the resonant scanner assembly 64, 72 and window 48 are structurally coupled to move together along the azimuth path 76 and elevation path 78 to cause the oscillating laser beams 66–68 to move along therewith. In this manner, the oscillating laser beams are forced to move in azimuth with the movement of the scan head 12 to form the sinusoidal scan pattern shown at 74.

Also, in the present embodiment, the various scan motors for controlling the azimuth, elevation and oscillations of the laser beams within the scan head may include position sensing elements which generate analog signaling of the specific position of the laser beam in the controlled scan of the perimeter scan as is well known to all those skilled in the pertinent art, the significance of which being more fully explained herein below. As described above, such position signals are conducted back to the electronics module 20 for use in processing the laser echoes.

While the scan head 12 is described in FIG. 3 as utilizing a beam expander 60, it is understood that in some applications, the beam expander 60 may not be used, in which case, the pulsed laser beam exiting the fiber optic cable 16 may be guided directly to the oscillating mirror 64 over the path 62. The natural divergence of the laser beam as it exits the fiber optic cable 16 may provide a sufficient beam width. In some cases, a collimating lens may be configured at some distance in the path 62 to stop the beam expansion and collimate the beam to a desired beam diameter prior to oscillation. Also, the present invention may be embodied to include more than one scan head 12 mounted at different locations on the sensor platform. Depending on the application, some of the scan heads may use fewer optical elements and less scan angle than that described for the embodiment of FIGS. 2 and 3. It is also understood that the oscillation angle θ of the resonant scanner 64, 72 may be controllably varied to become narrower or wider for different views.

In the illustrations of FIGS. 4 and 5, the laser system 10 is disposed on a moving vehicle 80, by way of example, to emit its pulsed laser beam at a targeted area or scene forward of the vehicle 80 for the illumination thereof. More specifically, the scan head 12 may be mounted on the front end 82 of the vehicle 80 utilizing a suitable structural mounting 84 to permit the scan head 12 to scan the laser beam, denoted by the dashed lines, in azimuth and elevation with respect to the forward motion of the vehicle 80 as denoted by the arrowed line 86. The scan head 12 may be coupled to the modules 14 and 20 of the system 10 which may be disposed on the vehicle 80 as shown in FIG. 4.

t is understood that additional scan heads may be disposed on the vehicle 80 to scan different targeted areas or scenes about the vehicle in the same manner as described for the scan head 12 in the illustrations of FIGS. 4 and 5. Also, while the present embodiment includes a scan head 12 for illuminating the scene, it is further understood that the scene need not be illuminated by scanning, but rather by the movement of the vehicle itself. For example, the oscillating laser beam may illuminate a scene by being pointed in one direction and scanning the scene according to the movement of the platform on which it is mounted.

Figure 6:
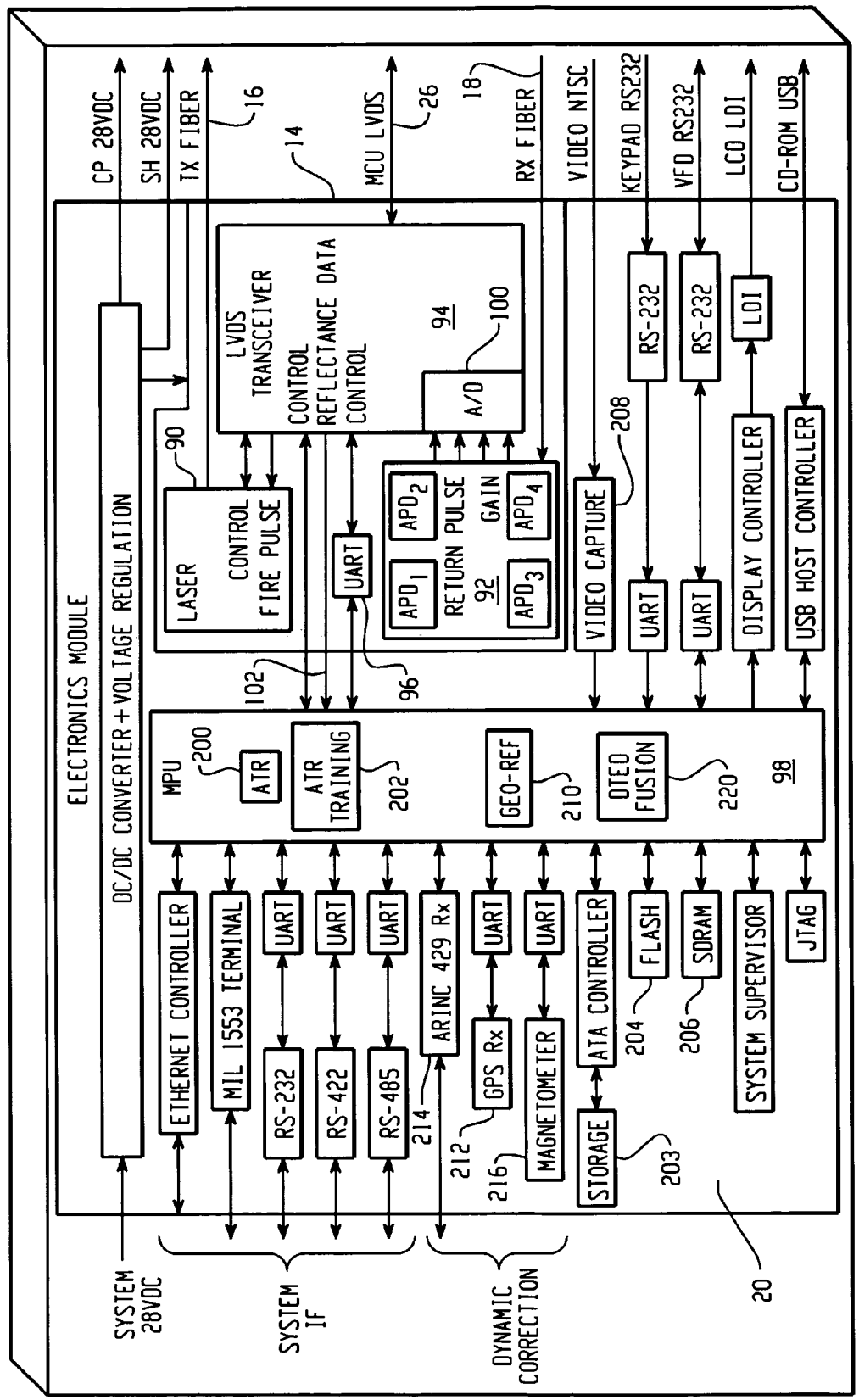
FIG. 6 is a functional block diagram of exemplary modules suitable for use in the laser system embodiment of FIG. 1.

FIG. 6 is a functional block diagram of exemplary modules 14 and 20 suitable for use in the laser system embodiment of FIG. 1. Referring to FIG. 6, the module 14 may include the functional blocks of a multi-spectral laser source unit 90, a multi-spectral laser return detector unit 92, a low voltage, differential signal (LVDS) transceiver unit 94 and a communication unit 96. All of the units of the module 14 may be powered by a 28 VDC electrical energy source generated within the module 20, for example. This same source may be used to power the motors and actuators of the scan head 12. The transceiver unit 94 receives control signals, either directly or through the communications unit 96, from a main processing unit (MPU) 98 of the module 20. These control signals may be used to pulse the plurality of lasers in laser unit 90 at a given pulse repetition rate, like on the order of 60 kHz or greater, for example, and to control the scan of the scan head 12 in azimuth and elevation, if desired. The scan head control signals are passed on-to the scan head 12 from the transceiver unit 94 over signal lines 26. Laser beam positional feedback signals in AZ and EL may be conveyed to the MPU 98 via the transceiver unit 94 from the scan head 12 over the signal lines 26.

Figure 7:
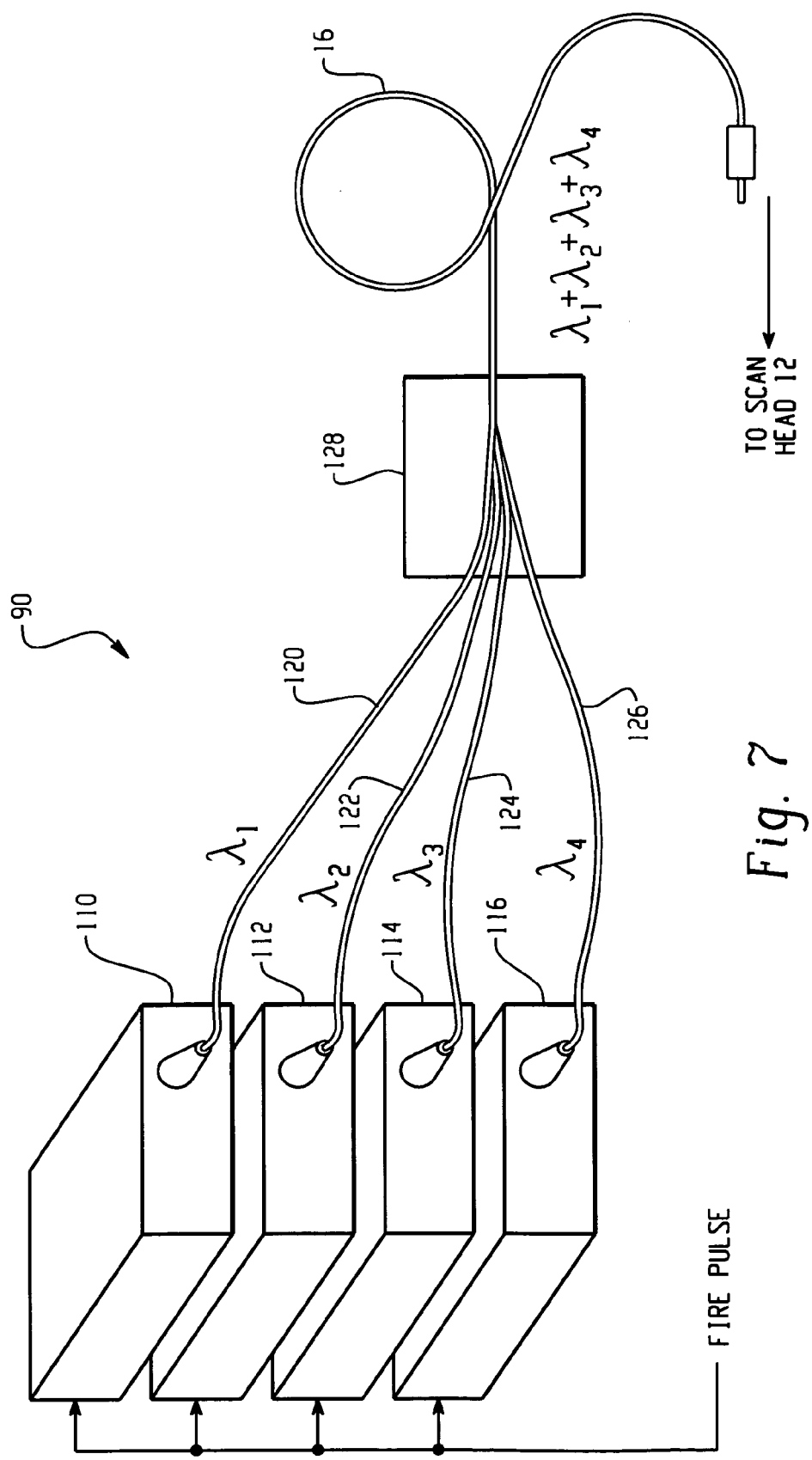
FIG. 7 is an illustration of an exemplary multi-spectral laser source unit suitable for use in the embodiment of FIG. 6.

FIG. 7 is an illustration of an exemplary multi-spectral laser source unit 90 suitable for use in the embodiment of FIG. 6. Referring to FIG. 7, the exemplary laser unit 90 comprises four laser sources 110, 112, 114 and 116, each tuned to emit simultaneously laser pulses at a different wavelength $\lambda 1$, $\lambda 2$, $\lambda 3$, and $\lambda 4$, respectively. In the present embodiment, the wavelengths $\lambda 1$, $\lambda 2$, $\lambda 3$, and $\lambda 4$ are selected preferably in the near IR range of approximately 1.06 to 2.0 microns, with at least one wavelength at 1.55 microns. Each of the laser sources 110, 112, 114, and 116 may be of the fiber laser type manufactured by IPG Photonics, bearing model no. ELPM-15K, for example. These type laser sources are based on fiber laser amplifiers using a MOPA architecture and operable to produce laser pulses of approximately 3–4 nanoseconds at approximately 15 kilowatts and at pulse repetition rates exceeding 60 kHz. Upon trigger, the pulse start times from the different lasers are preferably within 1–3 nanoseconds of each other.

The laser sources 110, 112, 114 and 116 may be pulsed simultaneously under control of the MPU 98 via a fire pulse signal to emit laser pulses to the scan head 12 over the common fiber optic cable 16. More specifically, laser outputs of the laser sources 110, 112, 114 and 116 are coupled respectively to fiber optic cables 120, 122, 124 and 126 which are coupled to four inputs of a 4:1 multi-mode fiber combiner 128. An output of the combiner 128 is coupled to one end of the common fiber optic cable 116 with the other end thereof coupled to the scan head 12. Accordingly, with each fire pulse signal, four pulses at wavelengths $\lambda 1$, $\lambda 2$, $\lambda 3$, and $\lambda 4$ are emitted simultaneously from the laser sources 110, 112, 114 and 116 over respective fiber optic cables 120, 122, 124 and 126 to the combiner 128. In combiner 128, the four pulses are combined and output simultaneously over fiber optic cable 16 to the scan head 12. The rate at which these pulses are simultaneously emitted may exceed 60 kHz.

Figure 8:
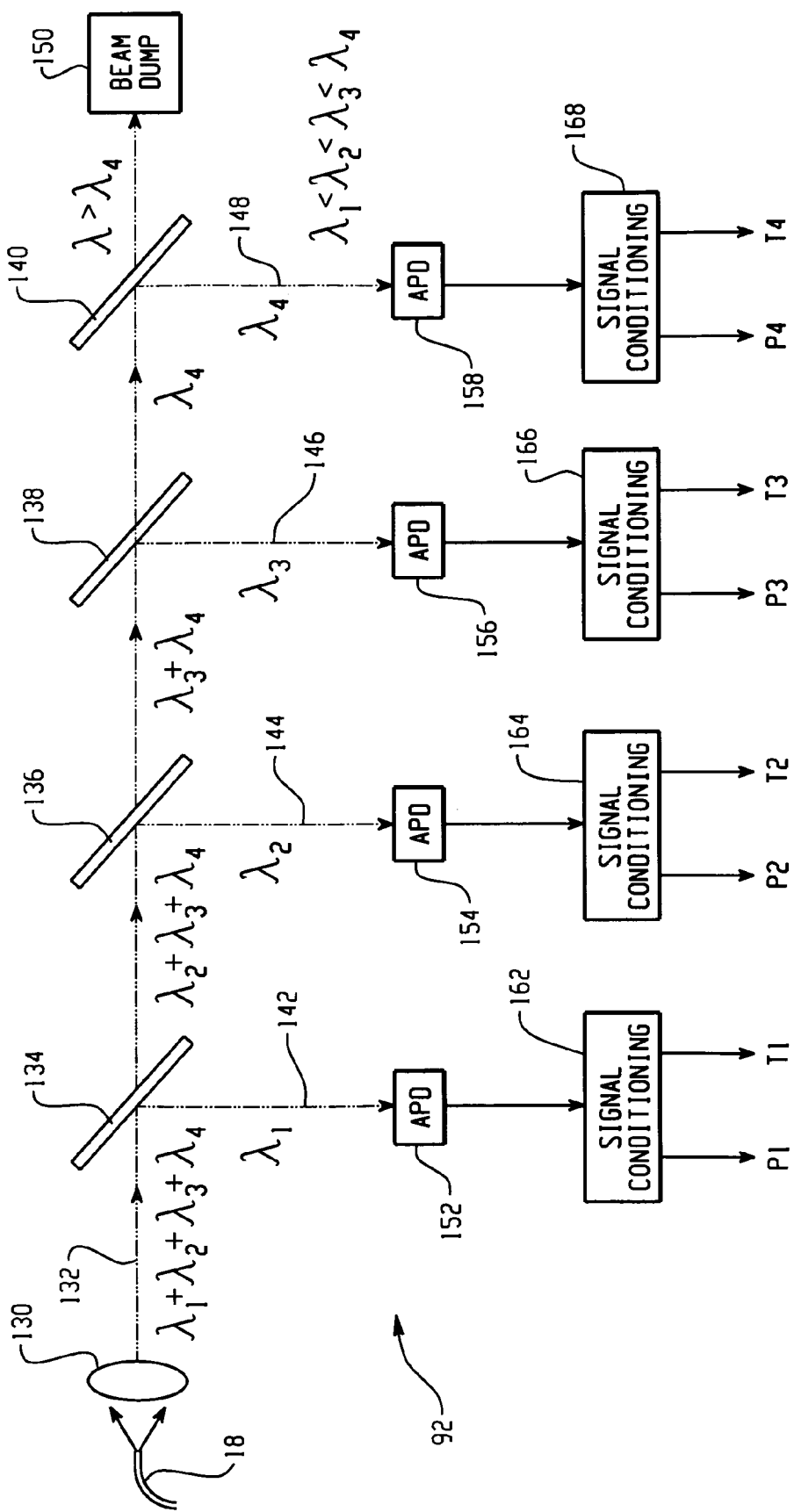
FIG. 8 is an illustration of an exemplary multi-spectral laser return detector unit suitable for use n the embodiment of FIG. 6.

Multi-spectral laser echo pulses are returned from the scan head 12 over the common fiber optic cable 18 to the detector unit 92 wherein the pulses are wavelength demultiplexed and distributed to corresponding light detectors which may be Indium Gallium Arsenide (InGaAs) avalanche photodetectors (APDs), for example. Each APD is preferably highly responsive at the multi-spectral set of wavelengths. FIG. 8 is an illustration of an exemplary multi-spectral laser return detector unit 92 suitable for use in the embodiment of FIG. 6. Referring to FIG. 8, in exemplary detector unit 92, multi-spectral laser return pulses output from cable 18 expand in beam width and are collimated by a collimating lens 130 which directs the return pulses over an optical path 132. Within the optical path 132 are disposed in series four dichroic long-wave bandpass filter optical elements 134, 136, 138 and 140, each of which being configured to reflect return pulses of only one of the wavelengths and pass the others.

For example, if $\lambda 1 < \lambda 2 < \lambda 3 < \lambda 4$, then optical filter element 134 may reflect only return pulses of wavelength $\lambda 1$ over optical path 142 and pass the return pulses of wavelengths longer than $\lambda 1$ over path 132; optical filter element 136 may reflect only return pulses of wavelength $\lambda 2$ over optical path 144 and pass the return pulses of the remaining wavelengths longer than $\lambda 2$ over path 132; optical filter element 138 may reflect only return pulses of wavelength $\lambda 3$ over optical path 146 and pass the return pulses of the remaining longer wavelengths over path 132; and optical filter element 140 may reflect only return pulses of wavelength $\lambda 4$ over optical path 148 and pass signals of any remaining wavelengths over path 132 to a beam dump 150. In this manner, the multi-spectral laser return pulses over cable 18 are demultiplexed and segmented into their individual wavelength components.

In the optical paths 142, 144, 146 and 148 are disposed APD light detectors 152, 154, 156 and 158, respectively, to receive the laser pulses of the individual wavelength components and convert them into corresponding electrical signals. The detector unit 92 further includes signal conditioning circuits 162, 164, 166 and 168 coupled respectively to the outputs of the APDs 152, 154, 156 and 158 to detect in real time a peak amplitude P1, P2, P3 and P4 for each discrete wavelength λ1, λ2, λ3, and λ4 of the multi-spectral set for each echo of an emitted multi-spectral laser pulse. These peak amplitudes are representative of the multi-spectral reflectance values for each laser pulse which represents a pixel of a laser scanned image. The signal conditioning circuits 162, 164, 166 and 168 also may generate trigger signals T1, T2, T3, and T4, respectively, for use in determining range of the object using time of flight (TOF) measurements.

Figure 9:
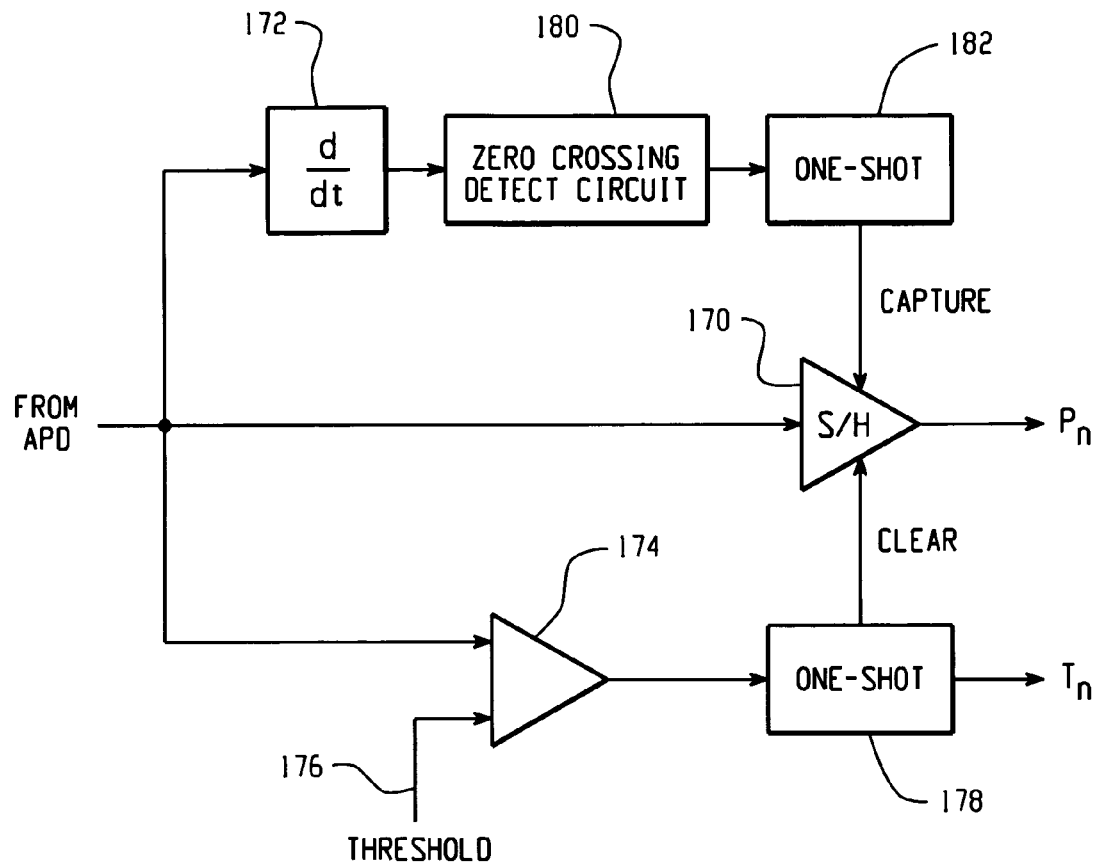
FIG. 9 is a block diagram schematic of an exemplary signal conditioning circuit suitable for use in the embodiment of FIG. 8.

FIG. 9 is a block diagram schematic of an exemplary signal conditioning circuit suitable for use in the detector unit embodiment described in connection with FIG. 8. Referring to FIG. 9, the output of an APD may be coupled to an input of a sample-and-hold circuit 170, an input of a differentiator circuit 172 and to one input of a threshold detector circuit 174. If the amplitude of the APD output signal is considered too low for processing, then an amplifier with filtering may be included for amplifying and filtering the APD output signal prior to coupling to the inputs of the circuits 170, 172 and 174. A predetermined threshold signal 176 may be coupled to another input of the detector circuit 174. The output of the detector circuit 174 may be coupled to a one-shot circuit 178 which generates a "clear" signal that is provided to the sample-and-hold circuit 170 and a "trigger" signal Tn that is passed on for a time of flight determination. Also, the output of the differentiator circuit 172 is coupled to an input of a zero crossing detect circuit 180, the output of which being coupled to another one-shot circuit 182. One-shot 182 generates a "capture" signal which is provided to the sample-and-hold circuit 170 which effects the peak pulse or reflectance value for the corresponding wavelength component.

In operation, as a converted return pulse of the corresponding wavelength component is received by its signal conditioning circuit, the circuit 174 detects the commencement of the pulse utilizing the predetermined threshold value and causes the one-shot 178 to generate a short pulse to clear the sample-and-hold circuit 170 and generate the trigger signal Tn. Once cleared, the circuit 170 tracks the amplitude of the return pulse. Concurrently, the circuit 172 differentiates the return pulse to generate a differential signal which is monitored by the zero crossing detect circuit 180. When the differential signal crosses zero potential indicative of the peak amplitude of the return pulse, the detector circuit 180 causes the one-shot 182 to generate a short pulse capture signal which forces the sample-and-hold circuit 170 to capture and hold the peak amplitude Pn of the return pulse which is provided at the output thereof. While the peak amplitudes of the return pulses are used to represent the reflectance values in the present embodiment, it is understood that other measurements, like the energy of or area under the return pulse, for example, may also be used to represent reflectance value just as well without deviating from the broad principles of the present invention.

It is recognized that a variation in timing known as "range walk" may be caused when a threshold detection circuit detects return pulses at different amplitudes. So, in an alternate embodiment to FIG. 9, the zero crossing signals may be enabled by the threshold signal to indicate the times of the returned pulses or to trigger signal Tn, thus eliminating much of the variation in timing caused by range walk.

In the present embodiment, the peak amplitudes P1, P2, P3 and P4 or reflectance data of the multi-spectral laser echo signals are captured and digitized in an analog-to-digital converter circuit (A/D) 100 which may be disposed in the transceiver unit 94, for example, and the digitized reflectance data is passed along in real time to the MPU 98 over data lines 102 along with their respectively corresponding trigger signals T1, T2, T3 and T4. The MPU 98 may compute in real time the range of the corresponding echo pulse from one or more of the trigger signals T1, T2, T3 and T4 utilizing time of flight techniques. Accordingly, multiple echoes from a common laser pulse may be range resolved or distinguished by range, through such time of flight calculations performed by the MPU 98. The MPU 98 will also receive in real time via transceiver 94 data corresponding to the position in AZ and EL of the laser pulse within the scan of the targeted area.

As the MPU 98 receives the multi-spectral reflectance data sets for each return pulse, a cube or array of digital data may be produced in real time sufficient to input to automatic target recognition (ATR) algorithm 200. In the present embodiment, the ATR algorithm 200 of the MPU 98 is embodied by an artificial intelligence neural network algorithm which may contain three or more levels, i.e. an input level of nodes, one or more middle levels of nodes and an output level of nodes. The neural network ATR algorithm 200 may be trained with an ATR training algorithm 202 utilizing basic training data including ground truth measurements as well as real-time updating and learning of new environments. Thus, when the system is deployed in a new geographic region, automated scanning and learning may occur utilizing the ATR training algorithm 202 to adjust the system to the surroundings. A user may select from a predefined set of material types to facilitate training and detection. Likewise, training sets for specific geographic regions may also be made available for user selection. All such training data may be stored in a storage memory 203, like a hard drive, a CDROM drive or other mass memory device, for example, which may be coupled to the MPU 98 through an ATA controller or USB host controller, for example.

More specifically, once the system is functionally operative, training of the ATR neural network algorithm may commence with ground truthing to establish a relevant relationship between measured multi-spectral reflectance data against known threats. Captured multi-spectral reflectance values will be used to train the neural network. This training may be accomplished on land features and large man-made objects on a laser radar test range, for example. As part of the training and adaptive retraining processes, a video camera may be bore-sighted with the direction of laser emissions so that the user may view the scene being scanned by the laser. In the present embodiment, images from the camera are provided to the MPU 98 by a video NTSC signal through a video image capture device 208. The video images captured by the MPU 98 may be displayed on a LCD via a display controller and LDI, for example. The user may identify objects, like ground features, for example, in the video image utilizing a cursor and keyboard data entry and/or a touch screen device or VFD. Such devices may provide object identification data for training purposes to the MPU 98 via a UART/RS-232 interface, for example.

Once the neural network is trained, new threats and datasets may be added and the neural network retrained as desired to build a knowledge base for the system which may be stored in the memory storage 203. Thus, the present system has the capability to be adaptively retrained or to reprioritize threats in near real time. For example, during field operations, intelligence may indicate that forces should be on the alert for a blue car (with a particular IR signature) containing occupants suspected of car-bombing intentions. These threat features may be provided as data inputs to the system to alert mobile forces for this key feature of interest by prioritizing the threat classification.

Various combinations of values derived from the four reflectance values for each return pulse may be used as additional inputs to the neural network ATR algorithm 200, such as various ratios, and averages, weighted means, standard deviations and other statistical components, for example. All told, there may be as many as twelve or more inputs to the neural network engine to render a better estimate of the material type associated with the reflectance value data set of each return pulse. Data may be normalized appropriately between the four channels to yield a better sensitivity in detection. A generic algorithm may be also used to achieve better performance. Thus, a digitally coded output representative of a material type may be generated by the neural network ATR algorithm 200 in real time for each return pulse. The MPU 98 correlates these material type coded outputs with their associated position and range data to assemble a scan image of material type pixels in real time. Where there is more than one return pulse per pixel in the image, the multiple return pulses are resolved in the image by their associated range values. In this manner, scan images of material types are formed in real time and stored in a temporary memory of the MPU 98 which may be a flash memory 204 or a SDRAM memory 206, for example, for threat detection and classification as will be described in greater detail herein below.

Because the active laser scanner or sensor of the present invention may be mounted on a moving vehicle, the motion and attitude of the sensor/vehicle should be taken into account in determining object perspective and motion between active synthetic images. Accordingly, real time coordinate transformations will be performed by a geo-reference algorithm 210 in the MPU 98 to compensate for motion and changes in spatial positioning of the active laser sensor between synthetic images. Of course, this compensation will not be needed for stationary laser sensing. Moreover, attitude compensation may not be needed if the laser sensing unit is mounted on the moving vehicle in a stabilized platform. Likewise, this processed data can be correlated spatially to a reference map or satellite image to provide a geo-located reference.

In the present embodiment, a global positioning system (GPS) receiver 212 may be used to provide real time sensor position data to the MPU 98 via a UART, inertial navigation system (INS) attitude data of the system may be afforded to the MPU 98 through an ARINC 429 receiver interface 214, and bearing of the sensor may be provided to the MPU 98 from a magnetometer 216 via another UART. Alternatively, position and vehicle attitude may be determined by triangulation of data from a plethora of GPS receivers dispersed at selected positions on the vehicle. The geo-reference algorithm 210 may receive and use the real time position and attitude data from the various aforementioned data input devices for compensating the multi-spectral reflectance data by referencing the multi-spectral reflectance data to a geo-located reference frame suitable for use on a moving ground vehicle or surface ship, for example. Using a DTED fusion algorithm 220, the resulting compensated material type image data may be merged with digital terrain elevation and/or geo-located background clutter data accessed from memory storage 203 in the geo-located frame of reference to further remove or augment land features and permit not only threat identification and classification based on material type on a pixel by pixel basis, but also range—resolved moving object indication while the laser sensor is in motion, as will become more evident from the following description.

Figure 10A:
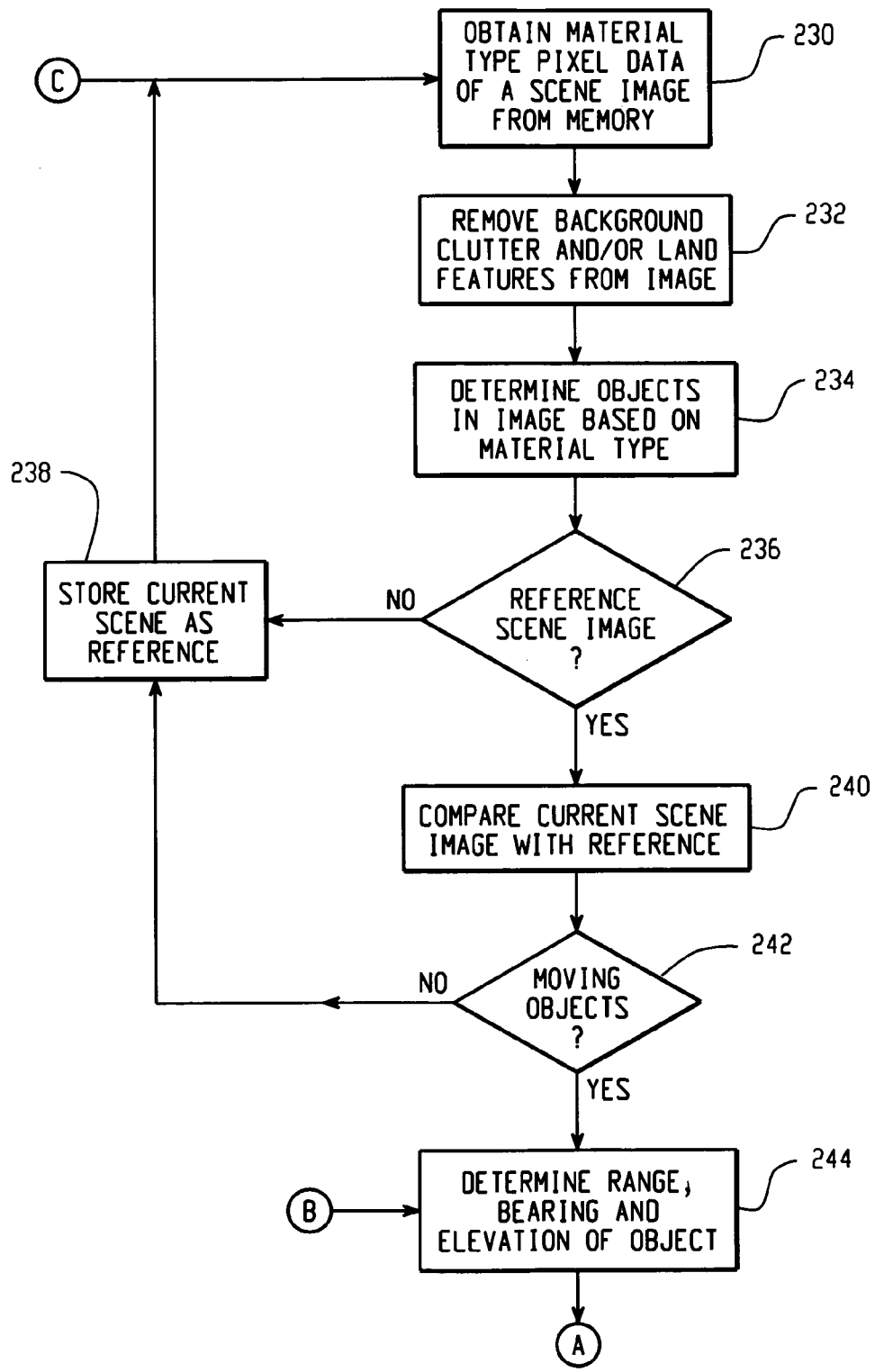
FIGS. 10A and 10B depict a flowchart of an exemplary algorithm suitable for use in the processing unit of the embodiment of FIG. 6.
Figure 10B:
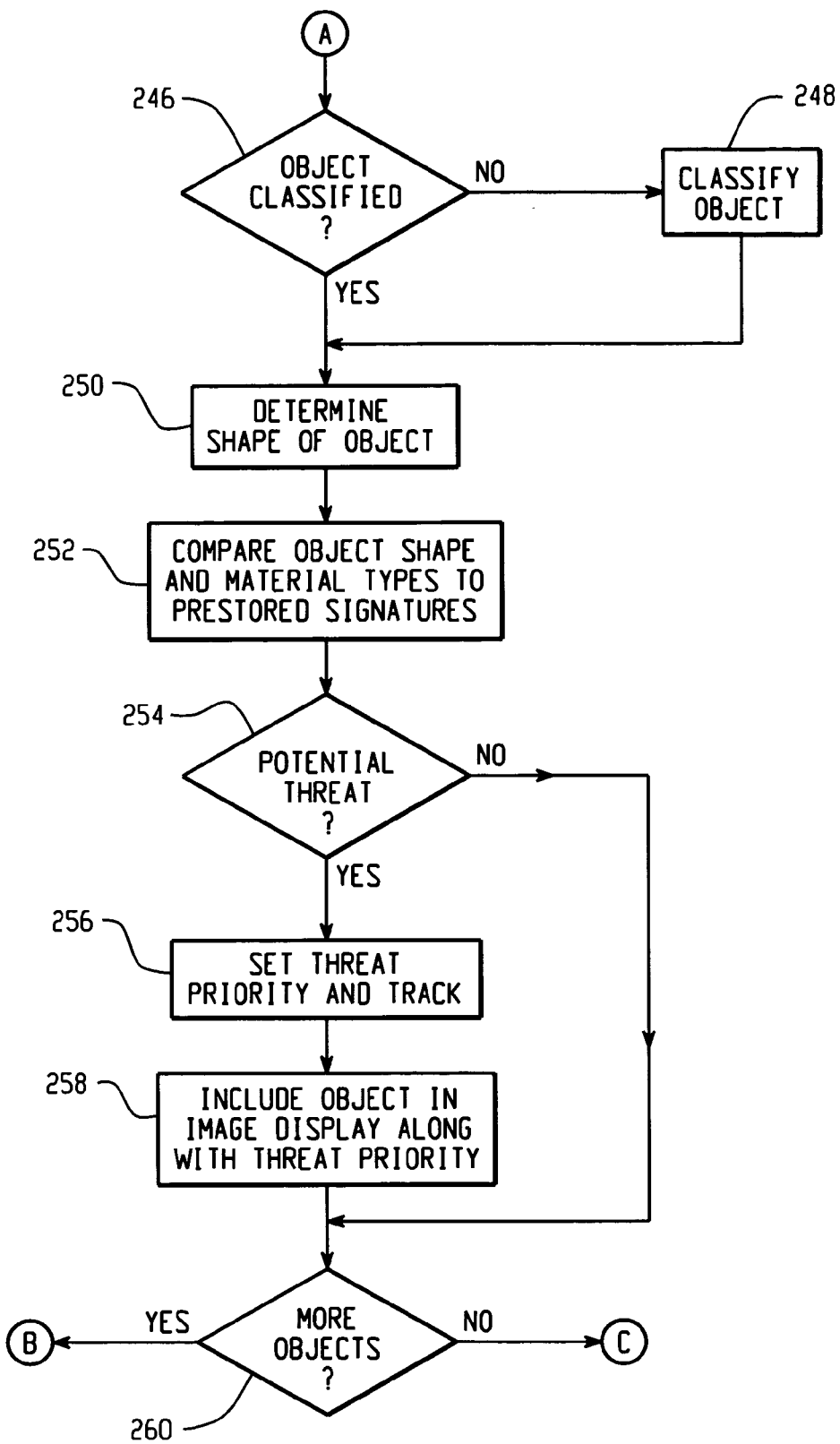

A flow chart of an exemplary algorithm which may be executed in the MPU 98 for further processing motion compensated material type image data to identify and classify threats is shown in the flow diagrams of FIGS. 10A and 10B. Referring to FIGS. 10A and 10B, in block or step 230, the algorithm obtains from memory material type pixel data of a scanned image produced by the active laser system as described herein above. If such data is produced from a moving vehicle, then the data will have been motion compensated and referenced to the coordinates of a common frame of reference. In block 232, background clutter and/or land features may be removed from the image, if desired, using pre-stored reference data in memory 203 as described above, leaving only objects of interest in the image, for example. In block 234, certain objects within the image may be determined based on material types. For example, adjacent pixels in the scene of the same material type or types and having a range within tolerance limits may be clumped together and considered as belonging to a common object. There may be a plurality of objects determined for a scanned image.

Next, in decisional block 236, it is determined if a reference scene image has been stored and classified as such. If not, then the object data of the current scene is stored in memory and classified as the reference scene data in block 238. Processing is then continued at block 230 wherein material type data of the next scene image is obtained from memory and blocks 232 and 234 repeated for such data. If block 236 determines that object data of a reference scene is available in memory, then the object data of the current scene is compared with object data of the reference scene in block 240 to determine if any of the objects are in motion. In the present embodiment, a scanned image of a targeted area may be produced every 0.5 seconds, for example. So, in block 240, it may be determined if an object changed position in the common reference coordinates between image frames and to classify such objects as moving objects.

In block 242, it is determined if there are any objects classified as moving in the current image scene. If not, processing is continued at block 238 which has been described above. If moving objects are determined to exist in the current image, then the algorithm selects an object and determines its range, bearing and elevation in the common reference coordinates. Then, in block 246, it is determined if the object has been classified based on material type or types, i.e. human, man-made, natural or the like, for example. If not, then the object is classified accordingly to material type or types in block 248. This classification process may include comparison with pre-stored material type signatures accessed from memory 203, for example. After the object has been classified, the shape of the object may be determined in block 250.

Thereafter, the shape and material type or types of the object may be compared with pre-stored threat signatures in memory 203 in block 252 to determine if the object is considered a potential threat. In block 254, it is determined if the object has been classified as a potential threat by block 252. If so, a threat priority and track of the object through subsequent images are established in block 256. Next, in block 258, an object image is overlaid in the video image of the LCD display via the display controller along with its threat priority. Thus, a user may be made aware of the threat potential, its priority and position in the image from the screen image of the LCD, for example.

After block 258 is executed or if the object is not considered a potential threat by block 254, it is determined if more objects are in the current object image by decisional block 260. If no more objects are present in the image, then processing will continue at block 230 to obtain data from memory for the next image. Otherwise, blocks 244 through 260 will be repeated for another object in the image until all the objects of the image are processed. Note that the processing of the algorithm of FIGS. 10A and 10B may be executed in the MPU 98 in the background to the real time execution algorithms of the ATR neural network 200 and geo-reference 210, for example.

Referring back to FIG. 6, the electronics module 20 may also include a variety of system interfaces. For example, the module 20 may interface with the control panel 30 through a MIL 1553 terminal interface, and to higher level or other controllers through an ethernet controller, a RS-232/UART interface, a RS-422/UART interface and a RS-485/UART interface.

In summary, the active laser system described herein above utilizes multiple, simultaneous active laser sources to illuminate a given scene. The reflected laser energy is independent of solar background, rendering the system a near ideal approach to day-night application. Further, the system does not require active calibration against a known infrared source to establish proper radiometric characteristics. As such, the data processing is simplified over passive systems, very light weight, and suitable for a wide range of threat detection and discrimination.

While the present invention is described above in connection with one or more embodiments, it is understood that this presentation is entirely by way of example with no intention of limiting the invention in any way. Accordingly, the present invention should not be limited by any of the embodiments presented above, but rather construed in breadth and broad scope in accordance with the recitation of the claims appended hereto.

What is claimed is:

1. Method of identifying an object in a laser beam illuminated scene based on material types, said method comprising the steps of:
   emitting a pulsed beam of laser energy, each beam pulse comprising a plurality of different discrete wavelength emission components;
   illuminating a predetermined scene with said pulsed beam of laser energy;
   receiving return laser pulses from objects within said illuminated scene, each return laser pulse comprising return components corresponding to the plurality of different discrete wavelength emission components;
   determining spectral reflectance values for said plurality of return components of each return laser pulse;
   determining a material type for each return laser pulse of said illuminated scene based on said plurality of reflectance values of the corresponding return pulse;
   indexing each determined material type to a position in said illuminated scene; and
   identifying an object in said illuminated scene based on material types and indexed positions thereof in said scene.

2. The method of claim 1 including the steps of:
   determining a range of each return laser pulse of the illuminated scene;
   associating the range of the return laser pulse with the material type thereof; and
   identifying an object in said illuminated scene based on material types and corresponding indexed positions and ranges thereof in said scene.

3. The method of claim 2 wherein the step of identifying the object includes joining together material types that are of a predetermined type, adjacent to each other in position, and fall within a predetermined range bin.

4. The method of claim 2 including the step of classifying the identified object based on the material type thereof.

5. The method of claim 4 including the steps of:
   determining the shape of the identified object; and
   detecting a potential threat based on the material type and shape of the identified object.

6. The method of claim 5 wherein the step of detecting a potential threat includes comparing the shape and material type of the object to predetermined threat signatures.

7. The method of claim 6 including the step of prioritizing the detected potential threat based on the step of comparing.

8. The method of claim 5 including the step of including a representative image of the detected threat in a display image in accordance with its position in the illuminated scene.

9. The method of claim 5 including repeating the steps of claim 1 for each of a subsequent plurality of scenes; performing the steps of claims 2, 4, and 5 for each subsequent scene of the plurality; tracking the potential threat through the subsequent plurality of scenes; and prioritizing said threat based on the track thereof.

10. The method of claim 1 wherein the step of emitting includes the steps of:
    simultaneously emitting a plurality of laser pulses of different discrete wavelengths; and
    combining the plurality of laser pulses into each beam pulse of laser energy.

11. The method of claim 1 wherein the step of illuminating includes scanning an oscillating laser beam across the predetermined scene.

12. The method of claim 1 wherein the step of determining spectral reflectance values includes the steps of:
    separating each return laser pulse by wavelength into the return pulse components of different discrete wavelengths; and
    determining a spectral value for each separated return pulse component.

13. The method of claim 12 including the step of: capturing a peak of each separated return pulse component as the spectral value thereof.

14. The method of claim 12 including the steps of:
    determining a time of arrival of each separated return pulse component; and
    determining a range of a return laser pulse based on the times of arrival of the separated return pulse components thereof.

15. The method of claim 1 wherein the step of determining a material type for each return pulse includes operating on the plurality of reflectance values of each pulse with a neural network algorithm.

16. The method of claim 1 wherein the step of determining a material type for each return pulse is performed in real time.

17. The method of claim 1 wherein the step of illuminating includes scanning an oscillating laser beam across the predetermined scene; and wherein the step of indexing includes the steps of:
  determining the position of each return laser pulse in the scan of the scene;
  associating said position of each return laser pulse with the material type thereof; and
  indexing each determined material type based on the associated position thereof in the scan of the scene.

18. The method of claim 17 including the steps of:
  scanning an oscillating laser beam across the predetermined scene from different geographical positions; and
  referencing the determined positions of the return laser pulses to a common frame of reference based on said different geographical scanning positions.

19. The method of claim 17 including the steps of:
  scanning an oscillating laser beam across the predetermined scene from different attitudes; and
  referencing the determined positions of the return laser pulses to a common frame of reference based on said different scanning attitudes.

20. A system for identifying an object in a laser beam illuminated scene based on material types, said system comprising:
  a laser source for emitting a pulsed beam of laser energy, each beam pulse comprising a plurality of different discrete wavelength emission components;
  a first arrangement of optical elements disposed in a path of said pulsed beam for illuminating a predetermined scene with said pulsed beam of laser energy;
  a second arrangement of optical elements for receiving return laser pulses from objects within said illuminated scene and separating each return laser pulse into return components corresponding to the plurality of different discrete wavelength emission components;
  a first processing circuit for receiving said return components, determining spectral reflectance values for said plurality of return components of each return laser pulse, and generating reflectance signals representative thereof; and
  a second processing circuit for receiving said reflectance signals and determining a material type for each return laser pulse of said illuminated scene based on said plurality of reflectance signals of the corresponding return pulse, said second processing circuit operative to index each determined material type to a position in said illuminated scene, and to identify an object in said illuminated scene based on material types and indexed positions thereof in said scene.

21. The system of claim 20 wherein the second processing circuit is operative to determine a range of each return laser pulse of the illuminated scene, to associate said range of the return laser pulse with the material type thereof, and to identify an object in said illuminated scene based on material types and corresponding indexed positions and ranges thereof in said scene.

22. The system of claim 21 wherein the second processing circuit is operative to identify the object by joining together material types that are: of a predetermined type, adjacent to each other in position, and fall within a predetermined range bin.

23. The system of claim 21 wherein the second processing circuit is operative to classify the identified object based on the material type thereof.

24. The system of claim 23 wherein the second processing circuit is operative to determine the shape of the identified object, and to detect a potential threat based on the material type and shape of the identified object.

25. The system of claim 24 wherein the wherein the second processing circuit is operative to detect the potential threat by comparing the shape and material type of the object to predetermined threat signatures.

26. The system of claim 25 wherein the second processing circuit is further operative to prioritize the detected potential threat based on the comparison of the shape and material type of the object to the predetermined threat signatures.

27. The system of claim 24 including a display; and wherein the second processing circuit is operative to control the display to include a representative image of the detected threat in a screen image in accordance with its position in the illuminated scene.

28. The system of claim 20 wherein the laser source comprises a plurality of lasers operative to simultaneously emit a plurality of laser pulses of different discrete wavelengths for each beam pulse of laser energy; and an optical combiner for combining each simultaneously emitted plurality of laser pulses into the corresponding beam pulse.

29. The system of claim 20 wherein the first arrangement of optical elements comprises an optical scanner for scanning an oscillating laser beam across the predetermined scene.

30. The system of claim 20 wherein the second arrangement of optical elements comprises optical elements for separating each return laser pulse by wavelength into the return pulse components of different discrete wavelengths and distributing said return pulse components along separate optical return paths; and wherein the first processing circuit comprises: a light detector disposed in each optical return path for converting the corresponding return pulse component into an electrical return pulse signal representative thereof; and a signal conditioning circuit for receiving the electrical return pulse signals and determining a spectral reflectance value for each return pulse signal.

31. The system of claim 30 wherein the signal conditioning circuit comprises a circuit for capturing a peak of each return pulse signal as the spectral reflectance value thereof.

32. The system of claim 30 wherein the signal conditioning circuit comprises a circuit for determining a time of arrival of each return pulse signal, and generating a time signal representative thereof; and wherein the second processing circuit is operative to receive the time signals for each return laser pulse and to determine a range of each return laser pulse based on said corresponding time signals thereof.

33. The system of claim 20 wherein the second processing circuit comprises a digital processor programmed with a neural network algorithm, said digital processor operative to receive the plurality of reflectance values of each laser return pulse and to determine a material type for each return pulse by processing the plurality of reflectance values of each laser return pulse with said neural network algorithm.

34. The system of claim 20 wherein the plurality of different discrete wavelengths of the emission components are chosen from wavelengths within a near infrared band.

35. The system of claim 33 wherein the digital processor is operative to receive the plurality of reflectance values of each laser return pulse and to determine a material type for each return pulse by processing the plurality of reflectance values of each laser return pulse with said neural network algorithm in real time.

36. The system of claim 20 wherein the first arrangement of optical elements comprises an optical scanner for scanning an oscillating laser beam across the predetermined scene, said scanner coupled to said laser source and second arrangement of optical elements by fiber optic cables.

37. The system of claim 36 wherein the second processing circuit is operative to determine the position of each return laser pulse in the scan of the scene, to associate the position of each return laser pulse with the material type thereof, and to index each determined material type based on the associated position thereof in the scan of the scene.

38. The system of claim 37 wherein the scanner is mountable on a moving platform for scanning the oscillating laser beam across the predetermined scene from different geographical locations; including means for determining said geographical locations of the moving platform; and wherein the second processing circuit is operative to reference the determined positions of the return laser pulses to a common frame of reference based on said determined geographical locations.

39. The system of claim 37 wherein the scanner is mountable on a moving platform for scanning the oscillating laser beam across the predetermined scene from different attitudes; including means for determining said different attitudes of the scanner; and wherein the second processing circuit is operative to reference the determined positions of the return laser pulses to a common frame of reference based on said determined attitudes.

40. The system of claim 20 wherein the second processing means is operative to receive reflectance signals of and determine a material type for each return pulse of a plurality of sequentially illuminated scenes, to index each material type of a scene of said plurality to a position in the corresponding scene, and to identify a common object in each scene of the plurality based on material types and indexed positions thereof.

41. The system of claim 40 wherein the second processing means is operative to determine movement of the common object between scenes of the plurality.

42. The system of claim 41 wherein the processing means is operative to track the moving object through the plurality of scenes, and to asses threat based on the track of the moving object.

43. The system of claim 43 wherein the near infrared band spans approximately one to two microns.

* * * * *

UNITED STATES PATENT AND TRADEMARK OFFICE
CERTIFICATE OF CORRECTION

| | | |
|---|---|---|
| PATENT NO. | : 7,026,600 B2 | Page 1 of 1 |
| APPLICATION NO. | : 10/789114 | |
| DATED | : April 11, 2006 | |
| INVENTOR(S) | : James R. Jamieson, Mark D. Ray and Clinton T. Meneely | |

It is certified that error appears in the above-identified patent and that said Letters Patent is hereby corrected as shown below:

Claim 43 was misprinted and should read as follows:

Column 20, line 19, "claim 43" should read --claim 34--.

Signed and Sealed this

Twenty-fifth Day of July, 2006

JON W. DUDAS
*Director of the United States Patent and Trademark Office*